United States Patent [19]
Nakai et al.

[11] Patent Number: 5,872,120
[45] Date of Patent: Feb. 16, 1999

[54] APOPTOSIS REGULATING COMPOSITION

[75] Inventors: Satoru Nakai; Koutoku Aihara; Hitomi Mori; Michiaki Tominaga, all of Tokushima; Masakazu Adachi, Gunma; Hiroyuki Ichikawa; Seiji Akamatsu, both of Tokushima; Fumio Saito, Gunma, all of Japan

[73] Assignee: Otsuka Pharmaceutical Co., Ltd., Tokyo, Japan

[21] Appl. No.: 854,074

[22] Filed: May 9, 1997

Related U.S. Application Data

[62] Division of Ser. No. 466,449, Jun. 6, 1995, Pat. No. 5,672,603, which is a continuation of Ser. No. 989,028, Apr. 30, 1993, abandoned.

[30] Foreign Application Priority Data

| Jul. 3, 1991 | [JP] | Japan | 3-162587 |
| Feb. 20, 1992 | [JP] | Japan | 4-33469 |
| Mar. 3, 1992 | [JP] | Japan | 4-45178 |
| Mar. 25, 1992 | [JP] | Japan | 4-100585 |
| Jul. 2, 1992 | [JP] | Japan | PCT/JP92/00841 |

[51] Int. Cl.$^6$ .......... A61K 31/495; A61K 31/50
[52] U.S. Cl. .......... 514/254
[58] Field of Search .......... 514/254

[56] References Cited

U.S. PATENT DOCUMENTS 4,415,572  11/1983  Tominaga et al. .......... 474/250

OTHER PUBLICATIONS

Sasayama et al, *Heat and Vessels*, 2(1):23–28 (1986).
Leuprasitsakul et al, *Endocrinology*, 128(6):2709–2714 (1991).
Berkow, *The Merck Manual of Diagnosis and Therapy*, 15th Ed., Merck Sharp & Dohme Research Laboratories, Rahway, N.J., pp. 1043–1050 (1987).
Bush et al, *Experimental Hematology*, 19(6):490 (1991).
Nakai et al, *Biomedicine & Pharmacotherapy*, 46(5–7):308 (1992).

*Primary Examiner*—Russell Travers
*Attorney, Agent, or Firm*—Sughrue, Mion, Zinn, Macpeak & Seas, PLLC

[57] ABSTRACT

An object of the invention is to provide an apoptosis regulating composition. According to the invention, an apoptosis regulating composition is provided which comprises, as an active ingredient, at least one carbostyril derivatives of general formula (1)

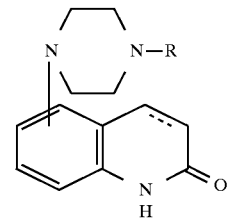

and salts thereof.

1 Claim, 12 Drawing Sheets

(×80)
control (×80)
AZ 30μg/ml

CMK day4
medium control (10%FBS)

CMK    day4
AZ (30μ/ml)

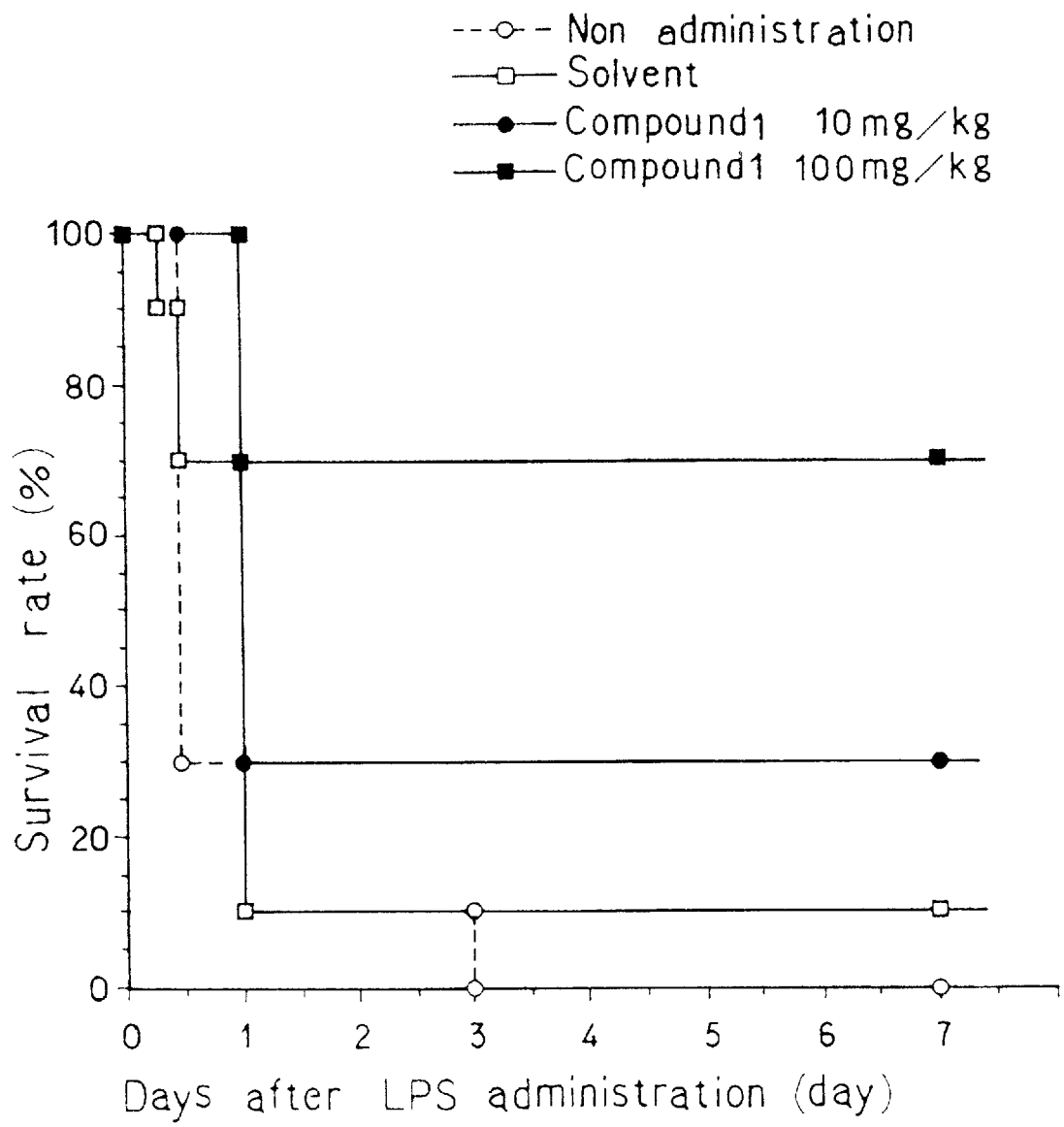

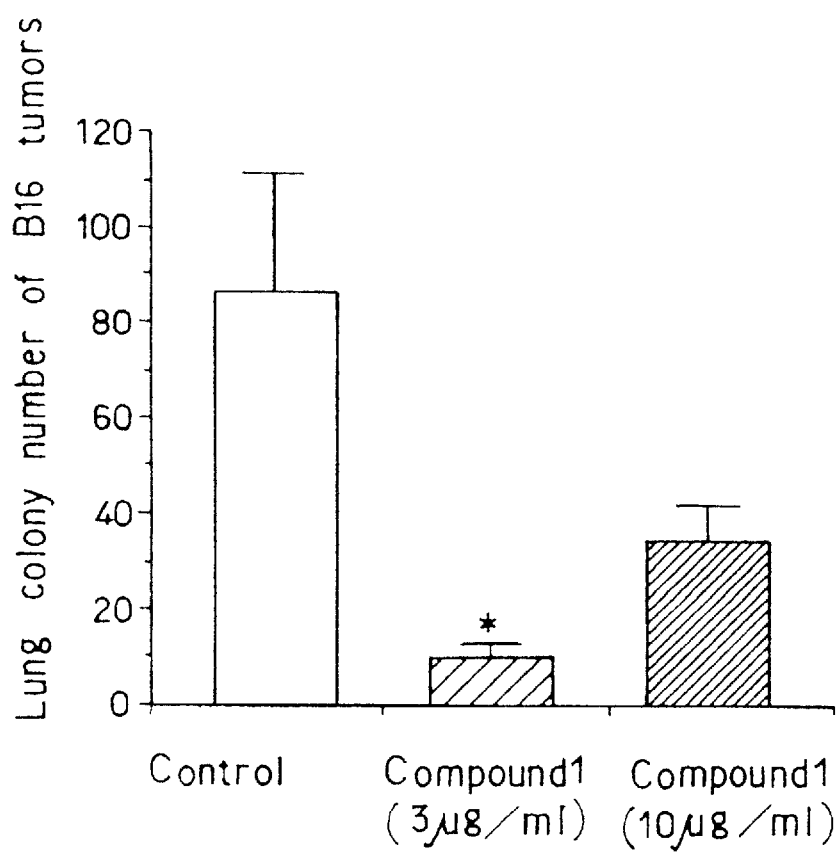

APOPTOSIS REGULATING COMPOSITION

This is a Divisional of Application Ser. No. 08/466,449, filed Jun. 6, 1995 (now U.S. Pat. No. 05,672,603; which in turn is a Continuation of Application Ser. No. 07/989,028, filed Apr. 30, 1993 (now abandoned).

The present invention relates to a novel apoptosis regulating composition.

The apoptosis regulating composition of the invention comprises, as an active ingredient, at least one member of carbostyril derivative represented by the following general formula (1) (hereinafter referred to as acompound (1)) and salts thereof.

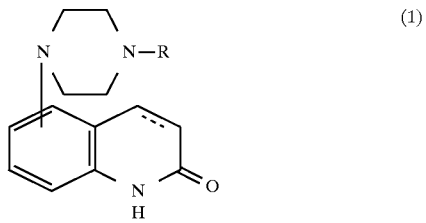

wherein R is a benzoyl group which may optionally have lower alkoxy groups on the phenyl ring as substituents and the carbon-carbon bond in the 3 and 4 positions of the carbostyril skeleton is a single bond or a double bond.

Regarding the above compound (1) and the processes available for production thereof, the descriptions in the Japanese Examined Patent Publication No. 43747/1989 (corresponding to U.S. Pat. No. 4,415,572)can be consulted. It is also known that the compound (1) is useful as cardiotonic.

The inventor of this invention did further research into the compound (1) and found that they have apoptosis regulating or modifying (suppressing or promoting) activity, including anticancer activity and cell differentiation inducing activity, among others, which can hardly be anticipated from their known activities mentioned above.

Meanwhile, it is said that two types of mechanism are involved in cell death. One is a classical type of cell death called necrosis. Morphologically, necrosis is characterized by marked swelling of mitochondria, swelling of cytoplasm and nuclear alteration, followed by cell destruction and autolysis. It occurs passively or incidentally. Tissue necrosis is generally caused by physical trauma to cells or a chemical poison, for instance.

Another type of cell death is called apoptosis (programmed cell death) [Kerr, J. F. R. and Wyllie, A. H., Br. J. Cancer, 265, 239 (1972)]. It is said that apoptosis can occur under various physiological conditions. Morphologically, apoptosis is characterized by loss of contact with neighboring cells, concentration of cytoplasm, endonuclease activity-associated chromatin condensation and pyknosis, and segmentation of the nucleus, among others. Disappearance of microvilli from the cell surface and smoothening of the cell surface (vesicle formation on the cell surface: membrane blebbing) are also observed. Fragmentation of the nucleosome unit of DNA into DNA fragments 180–200 bases in size due to endonuclease activation is further observable. Final fragments of apoptotic body cells are phagocytosed by neighboring cells. This is the mechanism discussed by Duvall and Wyllie [Duvall, E. and Wyllie, A. H., Immunology Today, 7 (4), 115–119 (1986); Science, 245, 301–305 (1989)]. Wyllie further reported that glucocorticoid-induced apoptosis of thymocytes involves intracellular endonuclease activation [Wyllie, A. H., Nature, 284, 555–556 (1986)]. Endonuclease activity causes fragmentation, to the oligonucleotide level, of DNA in cells undergoing apoptosis and this can be readily confirmed by agarose gel electrophoresis.

Apoptosis can be considered as preprogrammed cell death seen in the process of development, differentiation, or turnover of tissues [Wyllie, A. H., et al., Int. Rev. Cytol., 68, 251–306 (1980)].

In thymocytes, an increase in calcium level in the calcium ionophore or an increase in cAMP level leads to promotion of that DNA fragmentation which is characteristic of the above-mentioned apoptosis [Wyllie, A. H. et al., J. Pathol., 142, 67–77 (1984)] and, therefore, it is supposed that the calcium ion and/or cAMP be involved in the mechanisms of apoptosis. As an example so far reported, there may be mentioned apoptosis of HL-60 cells whose differentiation is induced by retinoic acid or the calcium ionophore [Martin, S. J., et al., J. Immunol., 145, 1859–1867 (1990); Martin, S. J. et al., Clin. Exp. Immunol., 79, 448–453 (1990)].

Reportedly, apoptosis occurs not only upon physiological cell death in the process of embryogenesis and physiological death of normal cells in active cell cycle (e.g. liver, adrenal cortex and prostate cells) but also is induced by glucocorticoid treatment, cell injury by cytotoxic T cells, atrophy of hormone-dependent tissues, irradiation, NE cells, killer cells, tumor necrosis factor (TNF), lymphotoxin (LT), other cytokines, etc. [Wyllie, A. H. et al., Int. Rev. Cytol., 68, 251 (1980); Duvall, E. and Wyllie, A. H., Immunology Today, 7, 115–119 (1986); Sellins, K. S., et al., J. Immunol., 139, 3199 (1987); Yamada, T., et al., Int. J. Radiat. Biol., 53, 65 (1988); Wyllie, A. H., Nature, 284, 555 (1980); Schmid, D. S., et al., Proc. Natl. Acad. Sci. USA, 83, 1881–1885 (1986); John, C., et al., J. Immunol., 129 (4), 1782–1787 (1982); Howell, D. M., et al., J. Immunol., 140, 689–692 (1988); Gillian, B., et al., Eur. J. Immunol., 17, 689–693 (1987)]. In addition, apoptosis is also inducible by some antibodies, for example anti-CD3, anti-APO-I, and anti-Fas antibodies [Trauth, B. C., et al., Science, 245, 301–305 (1989); Smith, C. A., et al. Nature, 337, 181–184 (1989); Tadakuma, T. , et al., Eur. J. Immunol., 20, 779 (1990)] and, further, apoptosis has been confirmed in the findings of Nakamura et al. as obtained in spontaneous regression of malignant tumor [Nakamura, Y., et al., Rinsho Hifuka (Jpn, J. Clin, Dermatol.), 35 (4), 289–295 (1981)].

On the other hand, actinomycin D (an RNA synthesis inhibitor), cycloheximide (a protein synthesis inhibitor) and calcium ion ($Ca^{2+}$) chelating agents, among others, have been reported as being capable of repressing apoptosis and, in addition, cyclosporin A (an immuno suppressant), hematopoietic system cytokines [IL-3, GM-CSF (granulocyte macrophage colony stimulating factor), G-CSF (granulocyte colony stimulating factor)], IL-2, bcl-2 gene product, and the like can reportedly repress apoptosis [Cohen, J. J., J. Immunol., 132, 38 (1984); Wyllie, A. H., et al., J. Pathol., 142, 67 (1984); Shi, Y., et al., Nature, 339, 625 (1989); Williams, G. L., et al., Nature, 343, 76 (1990); Nielo, M. A., J. Immunol., 143, 4166 (1989); Vaux, D. L., et al., Nature, 335, 1440 (1988)]. While, for cycloheximide and actinomycin D, there is a report describing apoptosis induction in acute leukemia cells by cycloheximide, in small intestine crypt cells by actinomycin D, and in HL-60 cells by both [Martin, S. J., et al., J. Immunol., 145, 1859–1867 (1990)]. On the other hand, it is reported that cycloheximide rather suppresses, and actinomycin D potentiates, apoptosis of the lymphocytic tumor cells which are present before X-ray radiation and are increased by X-ray radiation. Therefore, it is suggested that the kind of cells, conditions, and other mechanisms be involved in the suppression or promotion of apoptosis [Igarashi, T., et al., Nippon Ketsueki Gakkaishi (Acta Hematol. Jpn.), 51 (2), 144 (1988)]. At any rate, it is currently considered that the differentiation, growth and maturation of cells are closely associated with apoptosis and that substances capable of playing some or other part in such cell differentiation, growth or the like are associated with apoptosis as well.

Recently, cancer treatment with anti-Apo-I antibody has been attempted as an apoptosis-related therapy. Among the myelodysplastic syndrome (MDS), refractory anemia (RA) and refractory anemia wiht ring sideroblast (RARS) in which pancytopenia is predominant should preferably be treated with a combination of retinoic acid or vitamin $D_3$, which is a differentiation inducer for hemopoietic cells, and GM-CSF or IL-3 as an apoptosis regulating agent which suppresses excessive apoptosis of platelet producing cells whereas, in RAEB (refractory anemia with excess of blasts) and RAEB-t (RAEB in transformation) in which blast cell growth is active, retinoic acid and vitamin $D_3$ are said to act as differentiation-inducing agents, which induce differentiation of blast cells into mature blood cells, and etoposide and aclarubicin are said to act as apoptosis regulating agents, which suppress blast cell growth (thereby promote apoptosis) [Shibuya, T., J. Clin. Exp, Med., 160 (5), 319–323 (1992)].

Murakami et al. reported that about half of transgenic mice expressing anti-erythrocyte autoantibody manifest autoimmune diseases as a result of loss of self tolerance and that this is due to deficiency in ability to eliminate autoantibodies producing cells as resulting from apoptosis induction by self antigen-autoantibody producing cells reactions as in normal mice [Murakami, M., et al., Nature, 357, 77–80 (1992)].

Watanabe-Fukunaga et al. suggest that, for MRL lpr/lpr mice, Fas molecules relating to apoptosis has abnormality and the nagative relation (apoptosis) mechanism of autoreactive T-cells does not work properly in thymus. Consequently, autoimmune disease occur [Watanabe-Fukunaga, R., et al., Nature, 356, 314–317 (1992)].

According to Montagnier et al., apoptotic DNA bands are observed in T lymphocyte extracts from HIV-infected patients. This phenomenon is observed in 90% of asymptomatic HIV-infected patients and in 100% of AIDS patients and of ARC (AIDS-related complex) patients, indicating increased apoptosis induction in HIV-infected patients as well [Montagnier, L., et al., Sixieme Colloque des Cent Gardes, 9–17 (1991)].

As regards development stage cell death in chickens, administration in advance of NGF (nerve growth factor; a protein that promotes cell hypertrophy and nerve fiber elongation in the nerve cell ganglion) can result in complete inhibition of nerve cell death in that development stage [Hamburger, V., et al., J. Neurosci., 1, 60 (1981)] while administration of an antibody to NGF conversely leads to loss of about 90% of juvenile sympathetic nerve cells [Levi-Montalchini, R. and Booker, B., Proc. Natl. Acad. Sci. USA, 46, 384 (1960)].

Clark classified spontaneous neuronal deaths into three types and identified type I as apoptosis since, in type I neuronal death, morphological characteristics are identical with those in apoptosis and since type I cell death, together with DNA fragmentation, is involved in the cell death caused by deprivation of the growth factor [Clark, P. G. H., Anat. Embryol., 181, 195 (1990); J. Neurosci., 1, 60 (1981); Proc. Natl. Acad. Sci. USA, 46, 384 (1960); Rawson, C. L., et al., J. Cell. Biol., 113, 671 (1991)].

According to a report by Edwards et al., NGF can inhibit programmed death of sympathetic nerve cells, hence NGF can presumably control apoptosis [Edwards, S. N., et al., J. Neurochemistry, 57 (6), 2140–2143 (1991)].

According to Fischer et al., aged rats with learning disorder, when administered with NGF, can recover from learning disorder as a result of said NGF acting on forebrain basal field cholinergic nerve cells which are known to be found damaged in Alzheimer's disease [Fischer, W., et al., Nature, 329, 65 (1987); Barde, Y.-A., Neuron, 2, 1525 (1989); Hatanaka, H., Develop. Brain Res., 30, 47 (1986); Hatanaka, H., et al., Develop. Brain Res., 39, 85 (1988)]. Hatanaka et al. suggest the possibility that NGF can be effective in differentiation, maturation, life supporting and prevention of aging, protect nerve cells from damaging, promote recovery of damaged nerve cells and inhibit nerve cell death in nervous diseases associated with aging of the brain, in particular in Alzheimer's disease [Hatanaka, H., Taisha (Metabolism), 28, 891–899 (1991)].

For hepatic lesion of drug resistant virus hepatitis, acceleration of apoptosis which is direct or through the immune system, is considered to be involved in hepatic lesion.

On the other hand, it is known that, in the liver, mitogens induce the growth of hepatocytes to produce a hyperplastic state, and this state is normalized by falling off and necrosis, i.e. apoptosis, of hepatocytes [Kerr, J. F., et al., Br. J. Cancer, 26, 239–257 (1972)]. As far as the liver is concerned, apoptosis is observable in hepatic hyperplasia, hyperplastic tuberculation and hepatic cancer, among others [Columbano, A., et al., Lab. Invest., 52, 670–675 (1985); Columbano, A., et al., Am. J. Pathol., 116, 441–446 (1984)] while, according to Kerr et al., apoptosis is not accompanied by inflammation or fibroplasia [Kerr, J. F., et al., Lancet, 2, 827–828 (1979)].

In view of the reports cited above, the present inventors consider that patients with hepatitis, whether acute or chronic, may be cured when apoptosis is inhibited. They further consider that, in patients in the process of transition from chronic hepatitis to hepatic cirrhosis and further to hepatic cancer, apoptosis is in a controlled state and thus cytotoxic T cells can induce hepatocyte inflammation, followed by fibrosis, causing aggravation to hepatic cirrhosis and that, therefore, hepatitis might be suppressed and development into cirrhosis prevented when apoptosis is promoted.

The present invention provides an apoptosis regulating composition comprising, as an active ingredient, an effective amount of at least one of the compounds of general formula (1) and salts thereof in combination with a pharmacologically acceptable carrier therefor.

The apoptosis regulating composition of this invention can regulate or control apoptosis and, owing to this action, is effective in the medicinal field as an anticancer agent, antiretrovirus agent, and therapeutic agent for autoimmune diseases, for thrombocytopenia, for Alzheimer's diseases and for various types of hepatitis, tumor metastasis inhibiting agent etc., as mentioned hereinbefore.

In the general formula (1), the benzoyl group which may have lower alkoxy groups as substituents on the phenyl ring includes benzoyl groups having 1 to 3 straight-chain or branched $C_{1-6}$ alkoxy groups substituting the phenyl ring, such as benzoyl, 2-methoxybenzoyl, 3-methoxybenzoyl, 4-methoxybenzoyl, 2-ethoxybenzoyl, 3-ethoxybenzoyl, 4-ethoxybenzoyl, 4-isobutoxybenzoyl, 4-hexyloxybenzoyl, 3,4-dimethoxy-benzoyl, 3,4-diethoxybenzoyl, 3,4,5-trimethoxybenzoyl, 2,5-dimethoxybenzoyl, and so on.

Of the active ingredient compound (1) according to the invention, 6-[4-(3,4-dimethoxy-benzoyl) -1-piperazinyl]-3, 4-dihydrocarbostyril is most preferable.

The compound (1) which are to serve as active ingredients in accordance with the invention may readily form pharmacologically acceptable salts with conventional acids. As such acids, there may be mentioned inorganic acids such as sulfuric acid, nitric acid, hydrochloric acid and hydrobromic acid, and organic acids such as acetic acid, p-toluenesulfonic acid, ethanesulfonic acid, oxalic acid, maleic acid, fumaric acid, citric acid, succinic acid and benzoic acid. These salts can also be used as active ingredient compounds of the present invention, just as the free compounds of general formula (1).

The compounds (1) and salts thereof, can be generally formulated into the per se conventional pharmaceutical preparations. Such preparations are prepared using the conventional fillers, extenders, binding agents, moistening agents, disintegrating agents, surfactants, lubricants, and the like diluents or excipients. These pharmaceutical preparations may have various dosage forms selected according to the purposes of therapy, and typical examples thereof are tablets, pills, powders, solutions, suspensions, emulsions, granules, capsules, suppositories, injections (solutions, suspensions, etc.), and opthalmic solutions.

For the manufacture of tablets, a wide variety of carriers so far well known in this field can be used. Thus, use can be made of, for example, vehicles or excipients such as lactose, sucrose, sodium chloride, glucose, urea, starch, calcium carbonate, kaolin, crystalline cellulose and silicic acid, binding agents such as water, ethanol, propanol, simple syrup, glucose solution, starch solution, gelatin solution, carboxymethylcellulose, shellac, methylcellulose, potassium phosphate and polyvinylpyrrolidone, disintegrating agents such as dry starch, sodium alginate, powdered agar, powdered laminaran, sodium hydrogen carbonate, calcium carbonate, polyoxyethylene sorbitan fatty acid esters, sodium lauryl sulfate, stearic acid monoglyceride, starch and lactose, disintegration inhibitors such as sucrose, stearin, cacao butter and hydrogenated oils, absorption promoters such as quaternary ammonium bases and sodium lauryl sulfate, wetting agents or humectants such as glycerol and starch, adsorbents such as starch, lactose, kaolin, bentonite and colloidal silica, and lubricants such as refined talc, stearic acid salts, powdered boric acid and polyethylene glycol. When necessary, the tablets may further.be provided with a conventional coating to give, for example, sugar-coated tablets, gelatin-coated tablets, enteric-coated tablets, film-coated tablets, or double-coated or multilayer tablets.

For the manufacture of pills, a wide variety of carriers well known in the art can be used. Examples are vehicles or excipients such as glucose, lactose, starch, cacao butter, hardened vegetable oils, kaolin and talc, binding agents such as powdered gum arabic, powdered tragacanth gum, gelatin and ethanol, and disintegrating agents such as laminaran and agar.

For the manufacture of suppositories, a wide variety of carriers so far known can be used. As examples, there may be mentioned polyethylene glycol, cacao butter, higher alcohols, higher alcohol esters, gelatin and semisynthetic glycerides.

In preparing injections, the solutions or suspensions are preferably sterilized and are preferably isotonic with blood and, for preparing such dosage forms, all the diluents in conventional use in this field can be employed. Thus, for example, water, ethyl alcohol, propylene glycol, ethoxylated isostearyl alcohol, polyoxylated isostearyl alcohol and polyoxyethylene sorbitan fatty acid esters may be mentioned. In this case, the pharmaceutical preparations may contain sodium chloride, glucose or glycerol in an amount sufficient to give isotonic solutions. It is possible to add conventional solubilizing agents, buffers, soothing agents or local anesthetics, etc.

Furthermore, when necessary, the pharmaceutical preparations may contain coloring matters, preservatives, perfumes, flavoring agents, sweetening agents and the like as well as other drugs.

The proportion of the active ingredient compound in these pharmaceutical preparations of this invention is not critical but may suitably be selected in a wide range. Generally, however, the proportion is recommendably selected within the range of about 1 to about 70% by weight, preferably about 1 to about 30% by weight.

The route of administration of these pharmaceutical preparations of this invention is not critical, either, but is selected according to the dosage form, the patient's age, sex and other factors and the severity of the disease to be treated. Thus, for instance, when they are provided in the form of tablets, pills, solutions, suspensions, emulsions, granules or capsules, the preparations are administered orally. Injectable solutions are administered intravenously, either alone or in admixture with conventional fluids for parenteral infusion containing glucose, amino acids and so on. Where necessary, these solutions may also be administered as it is by the intra muscular, intradermal, subcutaneous or intraperitoneal route. Suppositories are administered rectally. Ophtalmic solutions are drop lotion in the eyes.

While the dosage of the above pharmaceutical preparations is dependent on the method of administration, the patient's age, sex and other background factors, severity of the disease and so on, it is generally recommended to administer about 0.5 to 30 mg, as the active ingredient, viz. compound (1), per kilogram body weight per day. The amount of the active ingredient to be contained in each dosage unit is about 10 to 1000 mg.

The diseases against which the apoptosis regulating composition of the present invention can be expected to-be effective based on the cell differentiation inducing and other activities thereof include, among others, cancer, AIDS, ARC (AIDS related complex), ATL (adult T cell leukemia), hairy cell leukemia, myelopathy (HAM/TSP), respiratory disorder (HAB/HABA), arthropathy (HAAP), uveitis (HAU), other HTLV-I (human T cell leukemia virus type I) related diseases, autoimmune diseases such as SLE (systemic lupus erythematosus), collagen diseases such as rheumatoid arthritis (RA), ulcerative colitis, Sjögren's syndrome, primary biliary hepatic cirrhosis, idiopathic thrombocytopenic purpura (ITP), autoimmune hemolytic anemia, maysthenia gravis, Hashimoto's disease, and insulin dependent (type I) diabetes mellitus. The apoptosis regulating composition of the invention is also applicable to various diseases accompanied by thrombocytopenia, for example myelodysplastic syndrome, periodic thrombocytopenia, aplastic anemia, idiopathic thrombocytopenia, disseminated intravascular coagulation, etc. The composition of the invention is further applicable to various other diseases including various types of hepatitis (such as types C, A, B, and F), Alzheimer's disease, myocarditis, ARDS (adult respiratory distress syndrome), infectious diseases, liver cirrhosis, prostatic hypertrophy, uterine myoma, bronchial asthma, arteriosclerosis, various congenital malformations, nephritis, senile cataract, chronic fatigue syndrome, and myodystrophia.

The apoptosis regulating composition of the present invention, when administered as an anticancer composition, for instance, induces differentiation of cancer cells, subsequently promotes or inhibits apoptosis induction or, directly promotes or inhibits apoptosis induction, and thereby produces an anticancer effect. In this case, the composition of the invention, irrespective of dosage form and/or route of administration, can be used in combination with one or more of various anticancer agents known as cancer chemotherapeutic agents and/or radiation therapy. The active ingredient compound of the invention which can produce an excellent anticancer effect can thus markedly promote the effect of the other anticancer agent or agents combinedly used, to produce a synergistic effect. Therefore, even when the partner anticancer agent or agents are used in doses much smaller than the usual doses, a satisfactory anticancer effect can be obtained, whereby the adverse effects of the partner anticancer agent or agents can be minimized. As such chemotherapeutic agents, there may be mentioned, for example, 5-fluorouracil (5-FU; Kyowa Hakko Kogyo), mitomycin C (Kyowa Hakko Kogyo), futraful (FT-207; Taiho Pharmaceutical), endoxan (Shionogi & Co.) and toyomycin (Takeda Chemical Industries).

When used in the treatment of thrombocytopenia, the apoptosis regulating composition of the invention can produce a cell differentiation induction promoting action and at the same time an apoptosis suppressing action in patients with MDS such as RA or RARS, thus stimulating proliferation of hemopoietic cells and causing normal differentiation and maturation. In patients with MDS such as RAEB or RAEB-t, administration of the composition of the invention can result in induced differentiation of blast cells and inhibition of blast cell multiplication, whereby proliferation of mature cells can be caused. The composition of the invention can further be expected to act on promegakaryocytes and megakaryocytes and promote their differentiation and maturation, thereby promoting thrombopoiesis.

For use in the treatment of thrombocytopenia, the apoptosis regulating composition of the invention can be used in combination with one or more other known drugs such as thrombopoiesis promoting agents to potentiate these partner drugs. Thus, in some instances, even when the partner drugs are used in fairly reduced doses, a satisfactory therapeutic effect can be produced and the adverse effects of said drugs can be thereby reduced.

The apoptosis regulating composition of the invention is useful also as a therapeutic and prophylactic agent for Alzheimer's disease. In this case, in patients with classical Alzheimer's disease or senile dementia of Alzheimer type, the composition of the invention exhibits an NGF-like action through inhibition of apoptosis, thus producing the above-mentioned therapeutic and prophylactic effects. Further, in that case, the composition of the invention can be used in combination with any of the conventional therapeutic agents for Alzheimer's disease such as cerebral circulation ameliorating agents and cerebral metabolic agents, whereby their effects can be promoted and their adverse effects reduced in some instances.

The apoptosis regulating composition of the present invention can be used as a cirrhosis preventive air agent which controls apoptosis in patients with drug-induced hepatitis or viral hepatitis to thereby manifest a therapeutic effect in hepatitis and prevent hepatocytes from fibrogenesis.

Some dosage form examples for the apoptosis regulating composition of the invention, and results of pharmaceutical studies on the active ingredient compounds are presented below.

In the following pharmacological test examples, the accompanying drawings are referred to, wherein;

BRIEF DESCRIPTION OF DRAWINGS

FIG. 11 is a graph which shows the effect on hepatic failure according to the pharmacological test example 12;

FIG. 12 is a graph which shows the effect of B12 melanoma cells on experimental model of pulmonary metastasis according to pharmacological test example 13.

Figure 1:
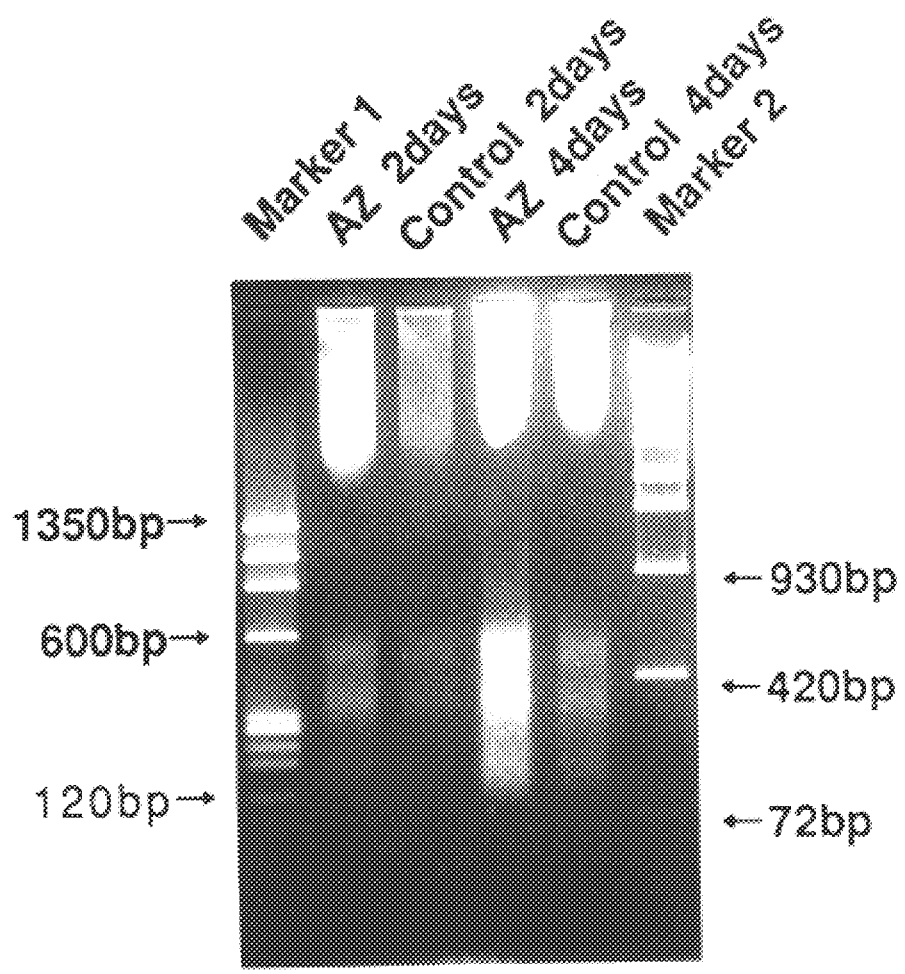
FIG. 1 shows DNA fragmentation results in the test of apoptosis regulating effect according to the pharmacological test example 1.

| Dosage Form Example 1 | |
|---|---|
| 6-[4-(3,4-Dimethoxybenzoyl)-1-piperazinyl]-3,4-dihydrocarbostyril | 150 g |
| Avicel (trademark, Asahi Chemical Industry Co., Ltd.) | 40 g |
| Corn starch | 30 g |
| Magnesium stearate | 2 g |
| Hydroxypropylmethylcellulose | 10 g |
| Polyethylene glycol 6000 | 3 g |
| Castor oil | 40 g |
| Methanol | 40 g |

The above active ingredient compound, Avicel, corn starch and magnesium stearate are mixed and ground together and the resulting mixture is compression-molded with a dragee R10 mm punch. The tablets thus obtained are coated with a film coating composition consisting of hydroxypropylmethylcellulose, polyethylene glycol 6000, castor oil and methanol to give film-coated tablets.

| Dosage Form Example 2 | |
|---|---|
| 6-[4-(3,4-Dimethoxybenzoyl)-1-piperazinyl]-3,4-dihydrocarbostyril | 150.0 g |
| Citric acid | 1.0 g |
| Lactose | 33.5 g |
| Dicalcium phosphate | 70.0 g |
| Pluronic F-68 | 30.0 g |
| Sodium lauryl sulfate | 15.0 g |
| Polyvinylpyrrolidone | 15.0 g |
| Polyethylene glycol (Carbowax 1500) | 4.5 g |
| Polyethylene glycol (Carbowax 6000) | 45.0 g |
| Corn starch | 30.0 g |
| Dry sodium lauryl sulfate | 3.0 g |
| Dry magnesium stearate | 3.0 g |
| Ethanol | q.s. |

The above active ingredient compound, citric acid, lactose, dicalcium phosphate, pluronic F-68 and sodium lauryl sulfate are admixed.

After size selection using a No. 60 screen, the mixture is granulated by the wet process using an alcoholic solution containing polyvinylpyrrolidone, Carbowax 1500 and Carbowax 6000. When necessary, alcohol is added to make the powder into a paste-like mass. Then, corn starch is added and the blending is continued until uniform granules are formed. The mixture is then passed through a No. 10 screen, placed in a tray and dried in an oven maintained at 100° C. for 12 to 14 hours. The dried granules are sieved through a No. 16 screen, then dry sodium lauryl sulfate and dry magnesium stearate are added and, after blending, the mixture is compressed to a desired size and shape using a tableting machine.

The above cores are treated with a varnish and dusted with talc for preventing absorption of moisture and then provided with an undercoat layer. Varnish coating is repeated as many times as sufficient for internal use. The tablets are rendered completely round and smooth by application of a further undercoat layer and a smooth coating. Coloring coating is conducted until a desired coloring is obtained. After drying, the coated tablets are polished to give uniformly polished tablets.

Pharmacological tests, described hereinafter, were performed using the following test compounds.

1. 6-[4-(3,4-Dimethoxybenzoyl)-1-piperazinyl]-3,4-dihydrocarbostyril
2. 6-[4-(3,4,5-Trimethoxybenzoyl)-1-piperazinyl]-3,4-dihydrocarbostyril
3. 7-[4-(3,4,5-Trimethoxybenzoyl)-1-piperazinyl]-3,4-dihydrocarbostyril
4. 7-[4-(3,4-Dimethoxybenzoyl)-1-piperazinyl]-3,4-dihydrocarbostyril
5. 6-[4-(4-Ethoxybenzoyl)-1-piperazinyl]-3,4-dihydrocarbostyril
6. 5-[4-(3,4-Dimethoxybenzoyl)-1-piperazinyl]-3,4-dihydrocarbostyril
7. 6-[4-(3,4-Dimethoxybenzoyl)-1-piperazinyl]carbostyril
8. 8-[4-(3,4-Dimethoxybenzoyl)-1-piperazinyl]-3,4-dihydrocarbostyril Pharmacological Test Example 1

Apoptosis-regulating effect

CMK cells were used to prepare a suspension of $1 \times 10^5$ cells/ml in RPMI-1640 medium supplemented with 10% fetal calf serum and Compound 1 was added at a concentration of 30 μg/ml. The mixture was incubated in a culture flask at 37° C. for 2 or 4 days. As a control, the medium to which the solvent alone was added was similarly incubated.

Cells were harvested by centrifugation at 4° C. for 10 minutes at 200×G. The pellet was dissolved in a hypotonic buffer (10 mM Tris-HCl, 1 mM EDTA and 0.2% Triton×100, pH 7.5) and the solution was centrifuged at 4° C. for 10 minutes at 13000×G. The supernatant was collected and allowed to stand in 50% isopropyl alcohol −0.5M NaCl at −20° C. overnight. The resultant precipitate was centrifuged at 4° C. for 10 minutes at 13000×G. the supernatant was discarded, and the sediment was dried. The dry sediment was resuspended in 10 mM Tris-HCl-1 mM EDTA (pH 7.4). To the supernatant was added RNase at a final concentration of 0.1 mg/ml and the mixture was incubated at 37° C. for 1 hour.

To a sample corresponding to the cell count of $1 \times 10^6$ was added ⅕ volume of a loading buffer containing 15 mM EDTA, 2% SDS, 50% glycerol and 0.05% bromphenol blue, and the mixture was incubated at 65° C. for 10 minutes.

The culture sample thus obtained was subjected to electrophoresis in 1.5% agarose gel at 100 V for 100 minutes. The DNA was stained with ethidium bromide.

The results are presented in FIG. 1.

In the figure, lanes at both sides represent markers 1 (120, 600 and 1350 bp) and 2 (72, 420 and 930 bp), respectively. The second lane from the left shows the pattern after 2 days of treatment with Compound 1, the third lane from the left the pattern after 2 days of control treatment, the fourth lane from the left the pattern after 4 days of treatment with Compound 1, and the fifth lane from the left the pattern after 4 days of control treatment.

It is, thus, clear that the expression of DNA fragments appears time-dependently on the electro-phoregram. This indicates that Compound 1 promotes apoptosis of CMK cells.

PHARMACOLOGICAL TEST EXAMPLE 2

Cancer cell growth inhibition (1) Human promyelocytic leukemia cells (HL-60)

The human promyelocytic leukemia cell line HL-60 is a human leukemia cell line established by Robert Gallo et al. and typical properties thereof are described in the literature [Gallo, R. C. et al., Blood, 54, 713 (1979)]. It is available from the American Type Culture Collection (ATCC) under the accession number ATCC No. CCL-240.

The concentration of HL-60 cells was adjusted to $1 \times 10^5$ cells/ml using RPMI-1640 medium (GIBCO) supplemented with 10% of FCS (fetal calf serum; GIBCO).

(2) Human stomach cancer cells (KATO-III)

The cell concentration was adjusted to $1 \times 10^5$ cells/ml using the same medium as used above in (1).

(3) Test compound solutions

Test compound 1 was dissolved in acetic acid, followed by dilution with the same medium as used above in (1) and neutralization with 2N NaOH to give final concentrations of 100 μg/ml, 10 μg/ml and 1.0 μg/ml.

(4) Giemsa stain solution

Giemsa stain solution was prepared by diluting Giemsa reagent (Merck) 50–100 times with phosphate buffer (pH 6.4).

(5) Esterase staining reagent

A reagent for esterase staining (Muto Kagaku) was used according to the naphthol AS-D chloroacetate method.

(6) Anti-CD33 monoclonal antibody My9

The monoclonal antibody My9 (Coulter) capable of specifically reacting with immature granulocytes was dissolved by adding 0.5 ml of distilled water per vial.

(7) Results a) The test compound solutions prepared as described above under (3) were added to the HL-60 cell suspension prepared as described above under (1) to final concentrations of 10 μg/ml and 1.0 μg/ml. Using 12-well culture plates (Costar), cultivation was conducted in a 5% carbon dioxide gas incubator maintained at 37° C. for 3 to 4 days. The test compound-free medium was used as a control. Thereafter, the cell suspension in each well was sampled and mixed with 0.2% trypan blue-containing phosphate buffer, and unstained viable cells were counted under a microscope. Based on the counting result, the viable cell concentration was readjusted to $1 \times 10^5$ cells/ml, and cultivation was continued under the same conditions.

The cell growth inhibiting effects on day 27 and day 33 are shown in Table 1.

KATO-III cells prepared as described above under (2) were cultivated in the same manner. The cell growth inhibiting effects on day 24 and day 33 are shown in Table 2.

TABLE 1

| Test compound 1 | Cell growth (%) On day 27 | Cell growth (%) On day 33 |
|---|---|---|
| 0 (Control) | 100 | 100 |
| 1.0 μg/ml | 76 ± 3.8 | 0 |
| 10 μg/ml | 54 ± 2.6 | 0 |

TABLE 2

| Test compound 1 | Cell growth (%) On day 24 | Cell growth (%) On day 33 |
|---|---|---|
| 0 (Control) | 100 | 100 |
| 1.0 μg/ml | 88 ± 2.3 | 0 |
| 10 μg/ml | 61 ± 1.5 | 0 |

From the data shown in Table 1 and Table 2, it is apparent that the growth of tumor cells is inhibited in a manner dependent on the concentration of the test compound.

b) Differentiation of HL-60 cells

HL-60 cells prepared as described above under (1) were cultivated in the same manner as in a). Cells collected on day 27 were placed on a slide glass and subjected to Giemsa staining, followed by morphological observation under a microscope. When the test compound was added, differentiation into cells with granule was observed as a morphological change as contrasted with the test compound-free case. The results of esterase staining by the naphthol AS-D chloroacetate method indicated differentiation of 70–85% of HL-60 cells into granulocytes.

c) Reactivity with anti CD33 monoclonal antibody My9

HL-60 cells prepared as described above under (1) were cultivated in the same manner as in a). On day 27, the cell concentration was adjusted to $1 \times 10^6$ cells/ml and 100 μl of each aliquot was reacted with 10 μl of fluorescein (FITC)-labeled My9, followed by flow cytometry. The positive rate data thus obtained are shown in Table 3.

TABLE 3

| Test Compound 1 | Positive rate (%) |
|---|---|
| 0 (Control) | 97 |
| 1.0 μg/ml | 90 |
| 10 μg/ml | 77 |

From the data shown in Table 3, it was noted that when the test compound was added, the proportion of undifferentiated HL-60 cells decreased while the proportion of differentiated cells increased.

The above results indicated that the active ingredient compound of the present invention has growth inhibiting and differentiation inducing effects on tumor cells.

PHARMACOLOGICAL TEST EXAMPLE 3

Differentiation inducing test (8) Monoclonal antibody FH-6

The monoclonal antibody FH-6 capable of recognizing sialyl LeX was fluoresein (FITC)-labeled, and the reactivity between the active ingredient compound of the present invention and FH-6 was examined by flow cytometry as follows.

(9) Reactivity with monoclonal antibody FH-6

The test compound solutions prepared as described above under (3) were added to HL-60 cells prepared as described above under (1) to a final concentration of 1.0 μg/ml or 10 μg/ml. Cultivation was conducted in a 5% carbon dioxide gas incubator at 37° C. for 2 hours. Thereafter, the cell concentration was adjusted to $1 \times 10^6$ cells/ml and 100 μl of each aliquot was reacted with 10 μl of the fluorescein-labeled FH-6 solution, followed by flow cytometry. The positive rate data thus obtained are shown in Table 4.

TABLE 4

| Test Compound 1 | Positive rate (%) |
|---|---|
| 0 (Control) | 95 |
| 1.0 μg/ml | 82 |
| 10 μg/ml | 76 |

From the above results, it was revealed that the addition of the active ingredient compound of the present invention resulted in loss of sialic acid from the HL-60 cell surface. This means differentiation of HL-60 cells and increase in sialidase activity.

PHARMACOLOGICAL TEST EXAMPLE 4

Effect on human promyelocytic leukemia cells (HL-60)

HL-60 cells were cultivated in RPMI-1640 medium supplemented with 10% of FCS at 37° C. under 5% $CO_2$, and the cell concentration was adjusted to $5 \times 10^4$ cells/ml.

Then, the above-mentioned medium containing 30 μg/ml of each test compound was added to each well of 6-well microplates (Costar), followed by 3 days of incubation at 37° C. under 5% $CO_2$. In a control group, the above medium alone was added and incubation was performed in the same manner. Thereafter, each cultured cell suspension was sampled into an Eppendorf tube and, after staining with 0.2% trypan blue-containing phosphate buffer, viable cells were counted using a hematocytometer.

The above cells were adjusted to $1 \times 10^7$ cells/ml. To 100 μl of the cell suspension was added 5 μl of a solution of fluorescein isothiocyanate (FITC)-labeled anti-human CD11b antibody (Mol; Coulter) and the reaction was allowed to proceed on ice in the dark for 30 minutes. Then, cells were washed twice with PBS (phosphate-buffered saline; Nissui Pharmaceutical) containing 0.1% of BSA (bovine serum albumin; Sigma), finally suspended in 500 μl of the BSA-containing PBS and measured for fluorescence intensity by flow cytometry using Profile II (Coulter).

The results thus obtained are shown in Table 5 and Table 6.

TABLE 5

| Test compound | Induction of differentiation promoting effect |
|---|---|
| 1 | 322 |
| 3 | 384 |
| 4 | 383 |
| 5 | 232 |
| 6 | 303 |
| 7 | 898 |
| 8 | 344 |

TABLE 6

| Test compound | Cell growth inhibiting effect (%) |
|---|---|
| 2 | 20.2 |
| 7 | 24.1 |
| 8 | 24.9 |

From data shown in the above tables, it was noted that, in test compound group, a cell growth inhibiting effect was produced while the expression of CD11b was increased whereby the induction of differentiation into the granulocyte, monocyte and macrophage series was promoted.

PHARMACOLOGICAL TEST EXAMPLE 5
M12 melanoma cell growth inhibition

This study was performed in groups of 10 Balb/c nude mice.

On the first day of the experiment (day 0), $2\times10^6$ M12 melanoma cells were transplanted into mice in the test group. When the tumor volume reached 100 mm$^3$, the test Compound 1 was administered orally in doses of 10 mg/kg daily to the mice. This treatment was carried out 30 times from day 25 to day 55. The tumor diameter was measured using calipers every day after transplantation of tumor cells. The tumor volume was calculated according to the following formula.

Tumor volume (mm$^3$)=(long diameter)×(short diameter)$^2$×½

Figure 2:
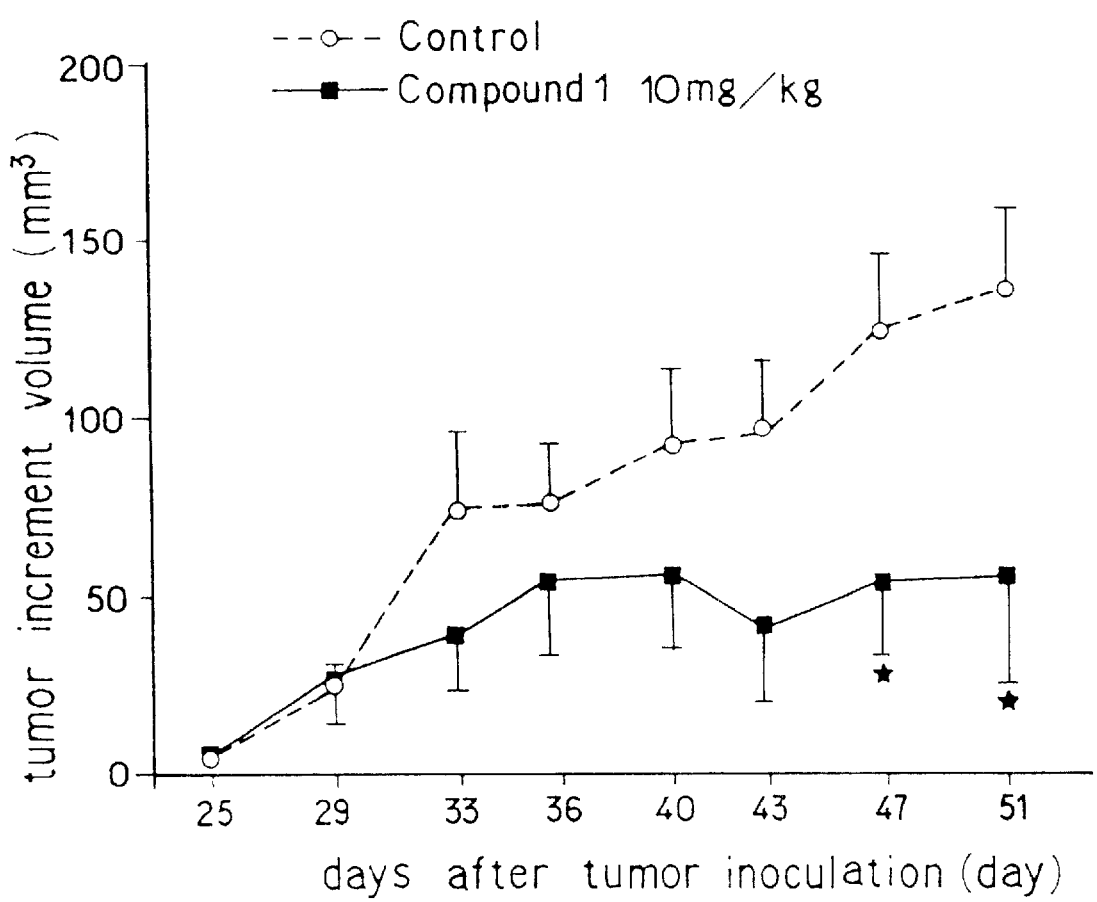
FIG. 2 is a graph which shows the results of M12 melanoma cell growth inhibition according to the pharmacological test example 5.

The results are shown in FIG. 2.

In FIG. 2, the corresponding results in the control group are also presented. In the figure, * indicates a significant difference at p<0.05 (Student's t test).

As seen from FIG. 2, the administration of the test compound significantly inhibits growth of M12 melanoma cells.

PHARMACOLOGICAL TEST EXAMPLE 6
ATL-infected cell growth inhibition

The following phamacological test was performed using Compound 1 as the test compound.

(a) Preparation of human peripheral blood acute lymphocytic leukemia cells (Molt-4)

Human peripheral blood acute lymphocytic leukemia cells (Molt-4) [J. Minowada, et al., J. Natl. Cancer Inst., 49, 891–895 (1972): ATCC CRL1582] were used to prepare a suspension of $1\times10^5$ cells/ml in RPMI-1640 medium (Gibco) supplemented 10% fetal calf serum (FCS, Gibco) for use as ATL virus-noninfected cells.

(b) Preparation of human adult T cell leukemic cells (5S)

Human adult T cell leukemia cells (5S) were used to prepare a suspension of $1\times10^5$ cells/ml in RPMI-1640 medium (Gibco) supplemented 10% fetal calf serum (FCS, Gibco) for use as ATL virus-infected cells.

(c) Preparation of the test compound

Compound 1 was dissolved in hydrochloric acid, diluted with the same medium as above, neutralized with 2N NaOH and adjusted to concentrations of 1 μg/ml, 10 μg/ml and 30 μg/ml.

(d) Pharmacological test

The cells prepared in (a) and (b) above were respectively placed in wells of a 24-well culture plate (Nunc), followed by addition of the test compound prepared in (c) (final concentration: 1 μg/ml, 10 μg/ml or 30 μg/ml), and cultured at 37° C. in a 5% carbon dioxide incubator for 4 days. As a control, the medium without addition of the test compound was used. After completion of incubation, the cell suspension in each well was taken for determination of viable cells.

The results are shown in Table 7.

TABLE 7

| Compound 1 (μg/ml) | 0 | 1 | 10 | 30 |
|---|---|---|---|---|
| Number of ATLV-noninfected cells (×10$^5$) | 13.9 | 13.9 | 12.2 | 12.8 |
| Number of ATLV-infected cells (×10$^5$) | 6.5 | 0.6 | 0.2 | 3.3 |

As seen from Table 7, the active ingredient compound of the invention (Compound 1) exerts a potent inhibitory effect on the growth of ATLV-infected cells at a concentration of at least 1 μg/ml, while it does not 5 affect ATLV-noninfected cells.

PHARMACOLOGICAL TEST EXAMPLE 7
Antiretrovirus activity test (a) Preparation of human transformed normal T cells (MT-4)

Human transformed normal T cells (MT-4) [Nagumo, T. and Hoshino, H., Jpn. J. Cancer Res. 79, 9–11 (1988)] were used to prepare a suspension of $2\times10^5$ cells/ml in RPMI-1640 medium (Gibco) supplemented 10% FCS (Gibco).

(b) Preparation of the test compound

Compound 1 was dissolved in hydrochloric acid, diluted in the same medium as above, neutralized with 2N NaOH and adjusted to concentrations of 1 μg/ml, 10 μg/ml, 30 μg/ml and 100 μg/ml.

(c) Phamacological test

The cells prepared in (a) above and the test compound (final concentration: 1 μg/ml, 10 μg/ml, 30 μg/mm or 100 μg/mm) prepared in (b) above were placed in the wells of a 12-well culture plate (Costar). Then, 50 μl/well of HIV suspension was added to infect the cells in each well, followed by 3-day incubation at 37° C. in a 5% carbon dioxide incubator. As a control, the medium without addition of the test compound was used. After completion of incubation, the cell suspension in each well was taken and viable cells were counted.

The cell suspension in each well was then centrifuged (1500 rpm×5 min) and 750 μl of culture supernatant was obtained.

The culture supernatant, 750 μl, obtained above was placed in an Eppendorf tube (1.8 ml) and 4M NaCl and PEG-6000 (Sigma) were added. The mixture was allowed to react at 0° C. for 2 hours to precipitate the virus and the virus was harvested by centrifugation (15000 rpm×20 min). To this virus pellet were added solution I [50% glycerol (Wako Pure Chemical), 25 mM Tris-HCl (pH 7.5), 50 mM KCl, 0.025% Triton X-100 (Sigma) and 5 mM DTT (Sigma)] and solution II [0.9% Triton X-100 (Sigma) and 1.5M KCl] for lysis at 0° C. for 30 min. To the resultant 10-μl virus solution were added 5 mg/ml bovine serum albumin (BSA, Sigma), 1M Tris-HCl, 100 mM DTT (Sigma), 1M KCl, 10 mM Poly A (Sigma), 0.15 mM TTP (Sigma), 200 mM MgCl$_2$, 0.15 mM Oligo(dT) (NEN) and [$^3$H]-TTP (NEN) and the mixture was allowed to react at 37° C. for 1 hour. The reaction was then stopped by placing the mixture in ice and the whole amount was spotted on a membrane filter (DE-81 Filter, Whatman) and dried. After drying, the filter was washed three times with 0.5M Na$_2$HPO$_4$ and rinsed in ethanol and dried. The radioactivity of [$^3$H]-TTP taken into DNA on the membrane was counted with a liquid scintillation counter to determine reverse transcriptase activity (unit, cpm).

The viable cell count ($\times 10^4$ cells) and reverse transcriptase activity (cpm) found as above are shown in Table 8.

TABLE 8

| Compound 1 (µg/ml) | 0 | 1 | 10 | 30 | 100 |
|---|---|---|---|---|---|
| Number of HIV-infected cells ($\times 10^4$) | 10.5 | 100 | 88 | 78 | 85 |
| Reverse transcriptase activity (cpm) | 1316 | 1423 | 1494 | 372 | 898 |

From Table 8, it was revealed that the active ingredient compound of this invention (Compound 1) not only inhibits cell growth but inhibits reverse transcriptase activity remarkably at doses of 30 µg/ml and 100 µg/ml.

The results of the above pharmacological test examples 6 and 7 demonstrate that the compound used as the active ingredient of this invention has high anti-retrovirus activity.

PHARMACOLOGICAL TEST EXAMPLE 8

Effect of the active ingredient compound of this invention in an animal model of autoimmune disease $W/BF_1$:(NZW×BXSB)$F_1$ mice are mice with spontaneous autoimmune disease. They are known as an animal model of lupus nephritis accompanied, with high frequency, by hypertension and myocardial infarction [Hang, L. M., et al., J. Exp. Med., 154, 216–221 (1981)]. They develop anti-platelet antibodies with increasing age, showing marked thrombocytopenia, and are used as an animal model of idiopathic thrombocytopenic purpura (ITP) as well [Oyaizu, N., et al., J. Exp. Med. 167, 2017–2077 (1988)]. It has been reported that more than 90% of the model animals die of myocardial infarction or renal failure within 8 months of birth [Ikehara, S., Metabolism and Disease, (Suppl) 26, 169–176 (1989)].

The life-prolonging effect of Compound 1 of this invention and the effects of the same compound on blood cells and anti-platelet antibodies were investigated in these $W/BF_1$:(NZW×BXSB)$F_1$ mice.

$W/BF_1$:(NZW×BXSB)$F_1$ mice were used at the age of 14 weeks (purchased from Kiwa Experimental Animal). Groups of 10 mice were used in each experiment.

The mice in respective groups were given a diet (Oriental Yeast),.which is usually given to this kind of mice, and water.

Compound 1 (Lot No. 9D87M) was used as suspended in a 0.5% solution of carboxymethylcellulose (CMC, Cellogen). Compound 1 was administered to mice by oral gavage in doses of 100 and 300 mg/kg body weight/day for 6 weeks from 14 weeks of age to 20 weeks of age according to the 5-day administration and 2-day cessation schedule. As a control, an untreated group was provided.

Figure 3:
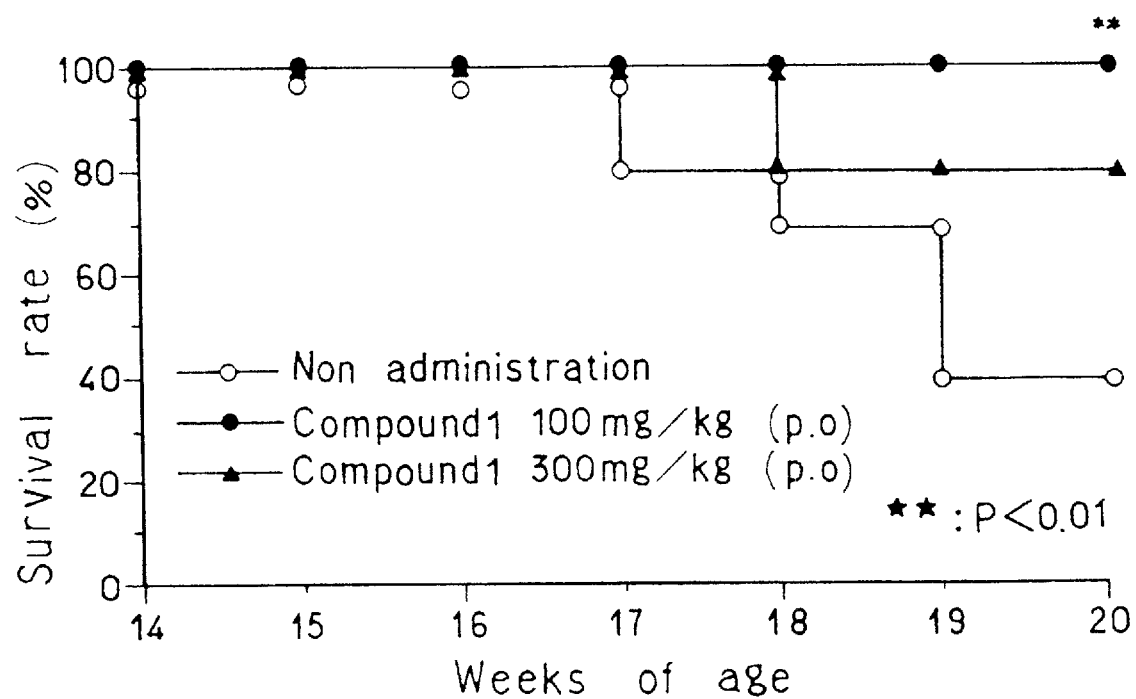
FIG. 3 is a graph showing the results of life-prolonging effect on autoimmune disease obtained by the pharmacological test example 8.

(1) For investigation of the-life-prolonging effect, the animals were observed for survival or death from 14 to 20 weeks of age. Statistic analysis was performed by the generalized Wilcoxon test with respect to the untreated group. The results are shown in FIG. 3.

In the figure, the ordinate represents the survival rate (%) and the abscissa represents the age in weeks (14 weeks to 20 weeks).

As seen from the figure, in the group given 100 mg/kg/day of Compound 1 of this invention, no death occurred till the age of 20 weeks. In the 300 mg/kg/day group, two animals were found dead at 18 weeks of age. In the untreated group, two, one and three animals were found dead at 17, 18 and 19 weeks of age, respectively. Thus, the life-prolonging effect of the active ingredient compound of this invention (Compound 1) in a mouse model of autoimmune disease was confirmed.

(2) For blood cell analysis, the blood was sampled from the fundus oculi at the age of 14, 16, 18 and 20 weeks. Changes in blood cell (white blood cell, red blood cell and platelet) counts were determined using an automatic blood cell analyzer (Coulter JR, Coulter). The differential (neutrophil and lymphocyte) counts were determined using blood smears stained with Wright-Giemsa stain. For statistical analysis, Student's t test was used, taking the untreated group as control, on each blood sampling day.

The results are shown in Table 9.

TABLE 9

| | | Weeks of age | | | |
|---|---|---|---|---|---|
| | Treatment | 14 | 16 | 18 | 20 |
| White blood cells ($\times 10^3/mm^3$) | Untreated | 8.23 ± 0.99 | 15.34 ± 4.53 | 10.87 ± 1.76 | 13.30 ± 4.04 |
| | Compound 1 100 mg/kg | 7.53 ± 1.26 | 12.91 ± 4.76 | 16.49 ± 4.98 | 11.72 ± 1.71 |
| | 300 mg/kg | 5.46 ± 0.74 | 9.36 ± 1.77 | 11.90 ± 3.52 | 12.97 ± 5.95 |
| Neutrophils ($\times 10^3/mm^3$) | Untreated | 2.06 ± 0.44 | 3.25 ± 1.90 | 2.38 ± 0.63 | 3.84 ± 1.86 |
| | Compound 1 100 mg/kg | 0.97 ± 0.21 | 3.01 ± 2.14 | 5.82 ± 1.65 | 3.25 ± 1.06 |
| | 300 mg/kg | 0.79 ± 0.19 | 1.86 ± 0.40 | 5.65 ± 2.77 | 2.24 ± 0.23 |
| Lymphocytes ($\times 10^3/mm^3$) | Untreated | 6.17 ± 0.92 | 12.06 ± 2.68 | 8.49 ± 1.39 | 9.47 ± 2.23 |
| | Compound 1 100 mg/kg | 6.55 ± 1.11 | 9.83 ± 2.72 | 10.68 ± 3.78 | 8.70 ± 1.02 |
| | 300 mg/kg | 4.50 ± 0.63 | 7.01 ± 0.92 | 6.16 ± 0.88 | 10.73 ± 5.81 |
| Red blood cells ($\times 10^6/mm^3$) | Untreated | 9.12 ± 0.53 | 7.82 ± 0.44 | 8.00 ± 0.60 | 6.80 ± 0.53 |
| | Compound 1 100 mg/kg | 9.08 ± 0.19 | 9.06 ± 0.19* | 8.46 ± 0.34 | 8.29 ± 0.37* |
| | 300 mg/kg | 9.17 ± 0.21 | 8.43 ± 0.30 | 8.83 ± 0.32 | 7.90 ± 0.30 |
| Platelets ($\times 10^3/mm^3$) | Untreated | 1144.5 ± 121.3 | 781.3 ± 115.5 | 670.3 ± 123.8 | 228.0 ± 90.0 |
| | Compound 1 100 mg/kg | 1225.2 ± 187.6 | 749.6 ± 116.6 | 524.0 ± 105.6 | 341.1 ± 111.9 |
| | 300 mg/kg | 1316.8 ± 86.3 | 1055.8 ± 72.0 | 980.0 ± 114.4 | 823.3 ± 24.5** |

*: $P < 0.05$
**: $P < 0.01$

As described in the above-mentioned report of Ikehara, the hematological feature of $W/BF_1$ mice is development of leukocytosis and thrombocytopenia with increasing age. In both the untreated group and the group given Compound 1 of this invention, the white blood cell count tended to increase with age, indicating that the compound of this invention has no effect on this parameter. The platelet count in the untreated control group began to decrease at 14 weeks of age (1144.5±121.3/mm$^3$) and, at 20 weeks of age, decreased to about one fifth (228.0±90.0/mm$^3$) the count found at 14 weeks of age. However, in the group given 300 mg/kg/day of the active ingredient compound of this invention (Compound 1), inhibition of decrease in platelet count began to appear immediately after initiation of treatment and a significant inhibition was found as compared to the untreated group (228.0±90.0/mm$^3$) at 20 weeks of age (823.3±24.5/mm$^3$). A similar result was found for red blood cell count.

(3) Oyaizu et al. have reported that in W/BF$_1$ mice, thrombocytopenia is associated with the appearance of anti-platelet antibodies. Since, as mentioned above in (2), the administration of Compound 1 of the invention inhibited a decrease in platelet count, the assay of anti-platelet antibodies was carried out at the age of 20 weeks.

The platelets collected from Balb/c mice and the plasma collected from W/BF$_1$ mice treated up to the age of 20 weeks were incubated together at room temperature for 30 minutes. The mixture was washed twice and allowed to react with FITC-labeled anti-mouse IgG (Tago, Code No. 6250), and after staining, anti-platelet antibodies were assayed with an FACS analyzer (EPICS-Profile II, Coulter). The negative control was set so plasma from Balb/c mice was 98% negative. The rate of each sample was determined.

The results are shown in Table 10.

TABLE 10

| | (% positive) | | |
|---|---|---|---|
| Mouse No. | Untreated | Compound 1 100 mg/kg | Compound 1 300 mg/kg |
| 1 | N.T | 3.7 | 2.3 |
| 2 | 20.9 | 13.5 | 11.4 |
| 3 | N.T | 3.1 | 14.1 |
| 4 | N.T | 17.3 | 6.0 |
| 5 | N.T | 21.5 | N.T |
| 6 | 26.0 | 16.8 | 16.4 |
| 7 | N.T | 18.2 | 12.1 |
| 8 | 27.9 | 7.8 | 4.1 |
| 9 | 3.7 | 8.5 | 19.5 |
| 10 | N.T | 27.1 | N.T |
| (Mean ± SE) | 19.6 ± 5.5 | 13.3 ± 2.7 | 10.7 ± 2.2 |

In the table, N.T. means "not tested" because of death at the time of determination. The numerical figures represent the positive rates (%).

The table shows that whereas the positive rate in the untreated group was 19.6±5.5%, the positive rate was 13.2±2.7% in the group given 100 mg/kg/day of the active ingredient compound of this invention (Compound 1) and 10.7±2.2% in the 300 mg/kg/day group, indicating a dose-dependent inhibition of anti-platelet antibodies.

As mentioned above, the W/BF$_1$ mouse is an animal model of spontaneous ITP for human chronic ITP. These animals develop lupus nephritis at or after 3 months of birth and more than 90% of them die of myocardial infarction or renal failure before 8 months of birth. It has been reported that these mice can be treated by transplanting bone marrow from normal Balb/c mice [Ikehara, S., et al., Proc. Natl. Acad. Sci. USA, 82, 2483–2487 (1985); Yasumizu, R., et al., Proc. Natl. Acad. Sci. USA, 84, 6555–6557 (1987); Ikehara, S., et al., Proc. Natl. Acad. Sci, USA, 56, 3306–3310 (1989)]. In clinical practice, too, the most effective treatment modality available today for ITP is considered to be bone marrow transplantation.

As seen from the results of above (1)–(3), the active ingredient compound of this invention exhibits a significant life-prolonging effect in W/BF$_1$ mice and inhibits thrombocytopenia due to appearance of anti-platelet antibodies, which is a hematological feature of this strain of mice, indicating that the compound has an autoimmune disease-improving effect.

PHARMACOLOGICAL TEST EXAMPLE 9

Thrombocytopenia-improving effect

1) Preparation of the test compound

Compound 1 was dissolved in 1N hydrochloric acid and diluted with fetal calf serum (FCS, Gibco) to give a 1 mg/ml solution. This solution was added to RPMI-1640 medium (Flow Laboratories) supplemented 10% FCS and the mixture was neutralized with 1N NaOH and adjusted to a concentration of 30 μg/ml before use.

2) Preparation of CMK cells

CMK cells were established by T. Sato et al. from patients with acute megakaryocytic leukemia. They are known to react with anti-platelet antibodies (anti-glycoprotein IIb/IIIa antibody, anti-glycoprotein Ib antibody and Plt-1 antibody). Moreover, it has mega-karyocyte-like properties, such as formation of α granules and a demarcation membrane in the cytoplasm. Therefore, these cells have been used for the analysis of the growth and differentiation of megakaryocytes [Sato, T., et al., Exp. Hematol., 15, 495 (1987); Sunami, S., et al., Blood, 70, 368 (1987); Komatsu, N., et al., Blood, 74(1), 42–48 (1989); Fuse, A., et al., British J. Haematology, 77, 32–36 (1991); Acta Haematologia Japonica 53(2), 294–295, 317–318 (1990)].

CMK cells were supplied by Dr. Takeyuki Sato at the Department of Pediatrics, Chiba University School of Medicine. The cells, 5×10$^4$ cells/ml, were cultured in RPMI-1640 medium supplemented 10% FCS and subcultured every four days.

3) Effect of Compound 1 on the expression of platelet-associated antigen of CMK cells CMK cells, 1×10$^5$ cells/ml, were incubated in 10% FCS-added RPMI-1640 medium, containing 30 μg/ml of Compound 1, for 4 days and the expression of platelet-associated antigen on the cell surface was determined by flow cytometry (Coulter) using FITC-labeled Plt-1 antibody (Coulter). The medium containing no Compound 1 was used as a solvent control.

For the analysis of cell surface antigen, 1×10$^6$ cells/100 μl of CMK cells were taken into a tube (Fischer) and reacted with 5 μl of FITC-labeled Plt-1 antibody at 4° C. for 30 minutes. The reaction mixture was washed three times with phosphate buffer containing 0.1% bovine serum albumin and determined for the percentage positive cells and fluorescence intensity.

The above-mentioned Plt-1 antibody (Coulter) is an antibody recognizing the platelet-associated antigen, glycoprotein IIb/IIIa and has been reported to increase with differentiation or maturation of CMK cells [Komatsu, N., et al., Blood, 74(1), 42–48 (1989)].

The results are shown in Table 11.

TABLE 11

| | | Plt-1 | |
|---|---|---|---|
| | Cell count (10$^5$/ml) | Percentage positive cells (%) | Mean fluorescence intensity (%) |
| Solvent control | 5.8 | 96.1 | 100.0 |

TABLE 11-continued

|  | Plt-1 | | |
|---|---|---|---|
|  | Cell count ($10^5$/ml) | Percentage positive cells (%) | Mean fluorescence intensity (%) |
| Compound 1 (30 μg/ml) | 3.2 | 96.5 | 191.6 |

The table shows that about 96% of CMK cells used are cells positive for the platelet-associated antigen recognized by Plt-1 antibody. The addition of 30 μg/mm of Compound 1 caused no change in the percentage of positive cells.

However, analysis of mean fluorescein intensity, which represents the amount of antigen expression per cell, shows that, with the mean fluorescein intensity of solvent control cells being taken as 100%, the intensity of the cells treated with 30 μg/ml of Compound 1 was about 191%. It is, thus, clear that addition of Compound 1 resulted in a 2-fold increase in the expression of platelet-associated antigen, recognized by Plt-1 antibody, on the surface of CMK cells.

4) Morphological observation of CMK cells

CMK cells, 1×$10^5$ cells/ml, were incubated in 10% FCS-added RPMI-1640 medium containing Compound 1 for 4 days and observed for the morphology of cells under the phase contrast microscope. A portion of the cell population was taken and a cytospin preparation was prepared and stained with Wright-Giemsa stain for determination of the cell morphology.

Figure 4:
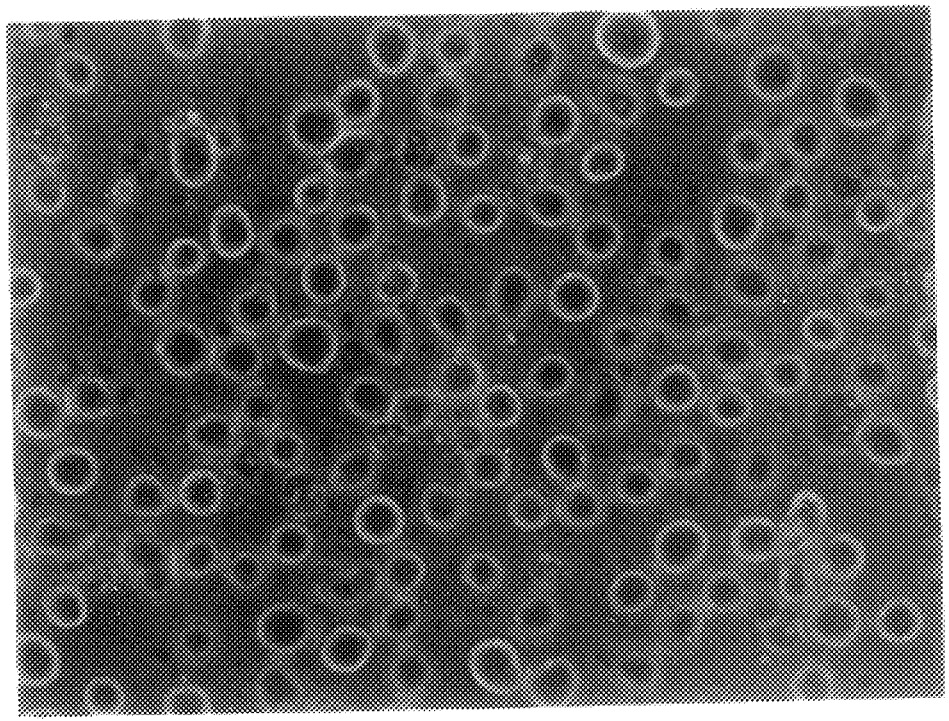
FIGS. 4 to 7 show the results of the thrombocytopenia-improving effect according to the pharmacological test example 9.
Figure 5:
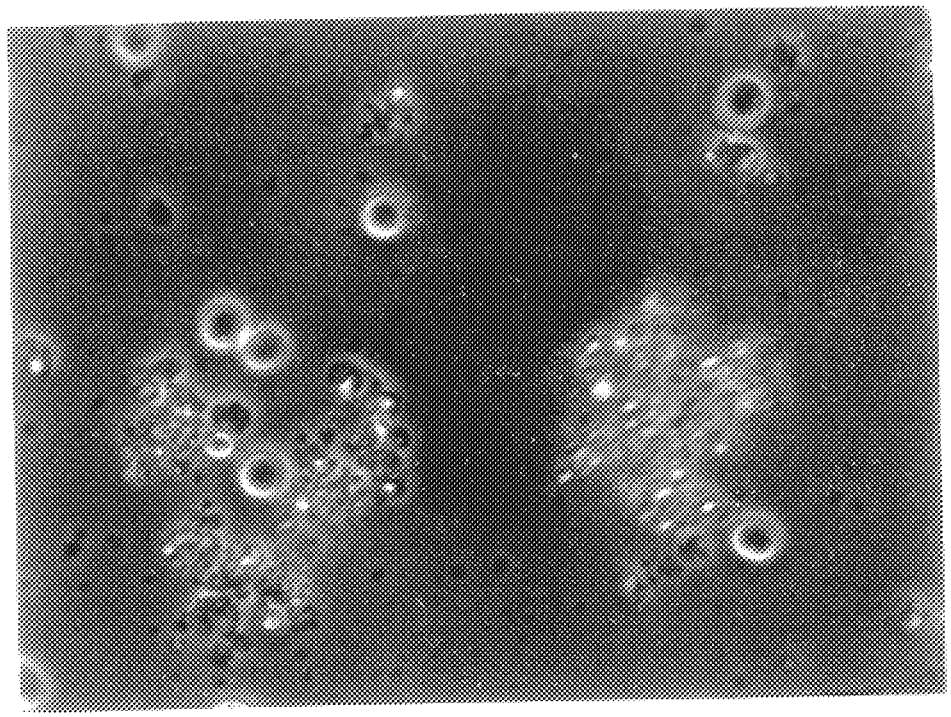
Figure 6:
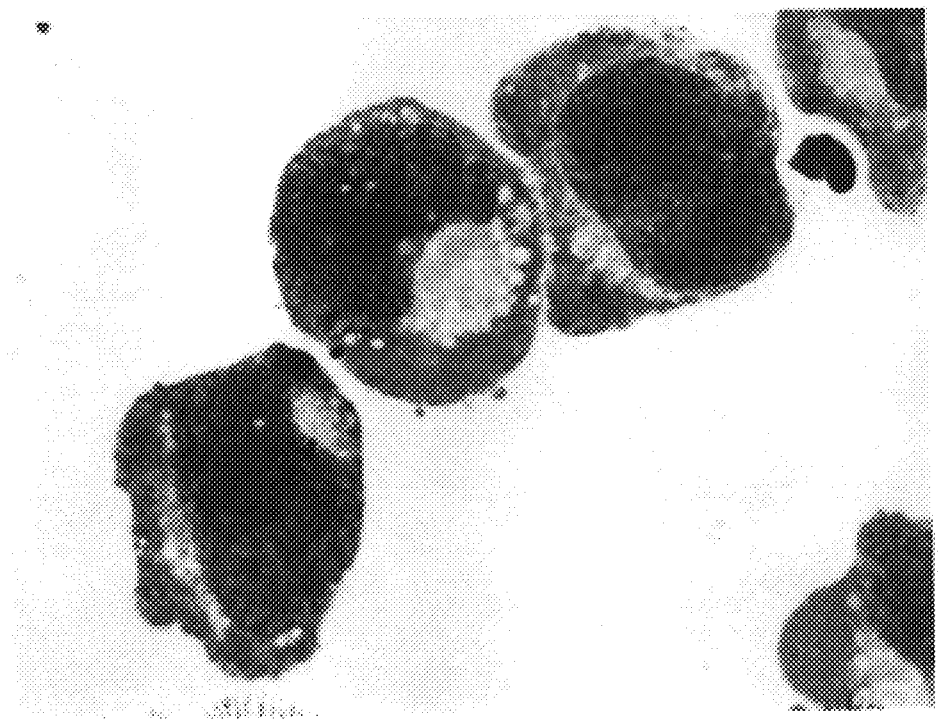
Figure 7:
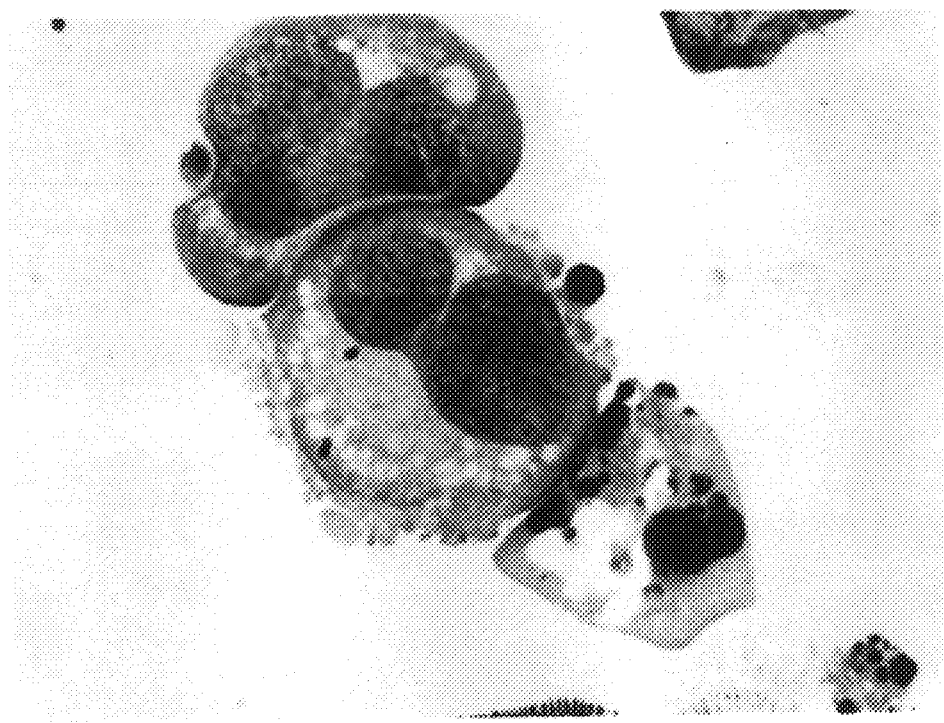
Figure 8A:
FIG. 8 shows the results of therapeutic effect on autoimmune disease according to the pharmacological test example 10.
Figure 8B:
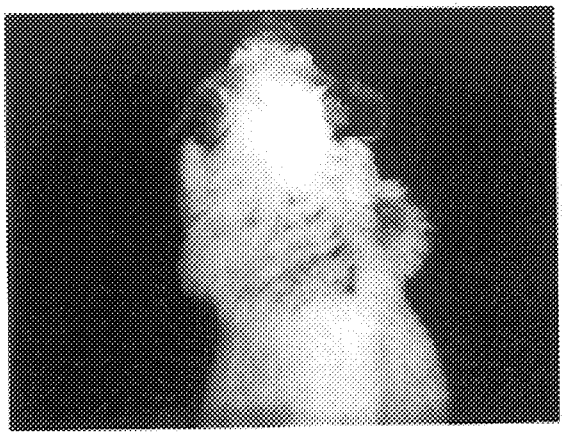
Figure 8C:
Figure 8D:

The results are presented in FIGS. 4–7. Thus, FIGS. 4 and 6 are the phase constrast micrograph and stained map, respectively, of the medium control, and FIGS. 5 and 7 represent the corresponding figures for cells treated with 30 μg/ml of Compound 1.

In the cells treated with 30 μg/ml of Compound 1 of this invention, the phase contrast micrograph reveals the fragmentation of cells like in the process of platelet production. The stained map shows budding of the cell membrane and lobulation of the nuclei in the cells treated with Compound 1 of this invention.

The foregoing results show that the carbostyril derivative, the active ingredient of this invention, increases the expression of platelet-associated antigen on the surface of CMK cells, causes fragmentation of cells like in the process of platelet production and further causes budding of the cell membrane and lobulation of the nuclei of cells and suggest that said compound promotes the differentiation or maturation of CMK cells. It is, therefore, expected that Compound 1 acts on promegakaryocytes or megakaryocytes to promote their differentiation and maturation by virtue of these characteristic actions and thereby stimulate platelet production and alleviate thrombocytopenia.

PHARMACOLOGICAL EXAMPLE TEST 10

Therapeutic effect on autoimmune disease

Groups of five female MRL/Mp-lpr/lpr mice (purchased at 7 weeks of age from Charles River Japan, Inc.) were used at the age of 19 weeks.

Mice of the above strain are known to spontaneously develop autoimmune diseases such as human systemic lupus erythematosus (SLE)-like immune complex glomerulonephritis, lymphoma, vasculitis and polyarthritis (Theofilopolos, A. and Dixon, F. J., Adv. Immunology, 37, 269 (1985); Murphy, E. D., Roths, J. B., Autoimmunity and lymphoproliferation, Elsevier North Holland, N.Y., 207–221 (1978); Taniguchi, Y., Gendai Iryo, 21, 131 (1989); Abe, C.).

Mice in both the Compound 1-treated group and the control group (untreated group) were given a mouse diet (Oriental Yeast) and water.

Compound 1 was used as suspended in 0.5% carboxymethylcellulose (CMC, Dai-ichi Kogyo Seiyaku Co., Ltd.) solution.

Compound 1 was administered by oral gavage in a dose of 300 mg/kg body weight daily from the age of 19 weeks to the age of 25 weeks according to the 5-day administration and 2-day cessation schedule (Compound 1-treated group).

Mice in the respective groups were examined for changes in urinary protein, lymphoma diameter, vasculitis of the auricle, and loss of hair.

As a result, the Compound 1-treated group -showed a tendency of inhibition of the increase in urinary protein as compared with the control group. As to lymphoma size, the diameter in the Compound 1-treated group was 7.8±1.3 mm vs. 9.0±0.8 mm in the control group, indicating that the enlargement of lymphoma was slightly inhibited.

FIG. 8 compares the degrees of vasculitis, hair loss and lymphoma between the groups.

The figure shows improvements in vasculitis and loss of hair and reduction in lymphoma in the Compound 1-treated group as compared to the control group.

The forgoing results indicate that administration of Compound 1 can be expected to ameliorate autoimmune disease on the basis of its apoptosis-modifying action.

PHARMACOLOGICAL TEST EXAMPLE 11

Effect on PC12 cells

PC12 cells subcultured in Dulbecco's modified Eagle's medium (D-MEM) supplemented with 5% heat-inactivated (56° C., 30 minutes) horse serum and 10% fetal calf serum (FCS) were transferred onto collagen-coated plastic Petri dishes (35 mm in diameter) at a concentration of 6×$10^4$ cells/3 ml medium. On day 2 of transfer, the culture medium was replaced with D-MEM supplemented with various concentrations of Compound 1, nerve growth factor (NGF, Wako Pure Chemical) or FCS (control) and culture was further continued. The cells were observed for morphological changes under the phase contrast microscope on day 3.

Figures 9A, 9B, 9C:
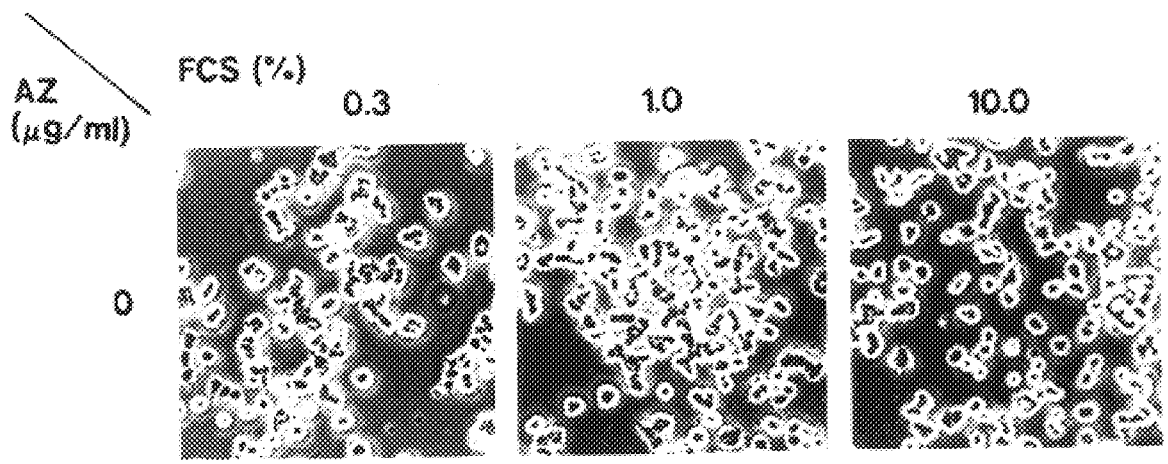
FIGS. 9 and 10 are photographs showing the effects on PC12 cells according to the pharmacological test example 11.
Figures 9D, 9E, 9F:
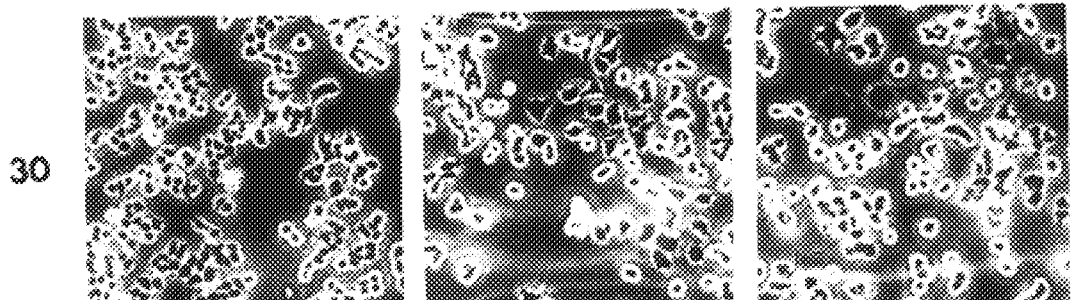
Figures 10A, 10B, 10C:
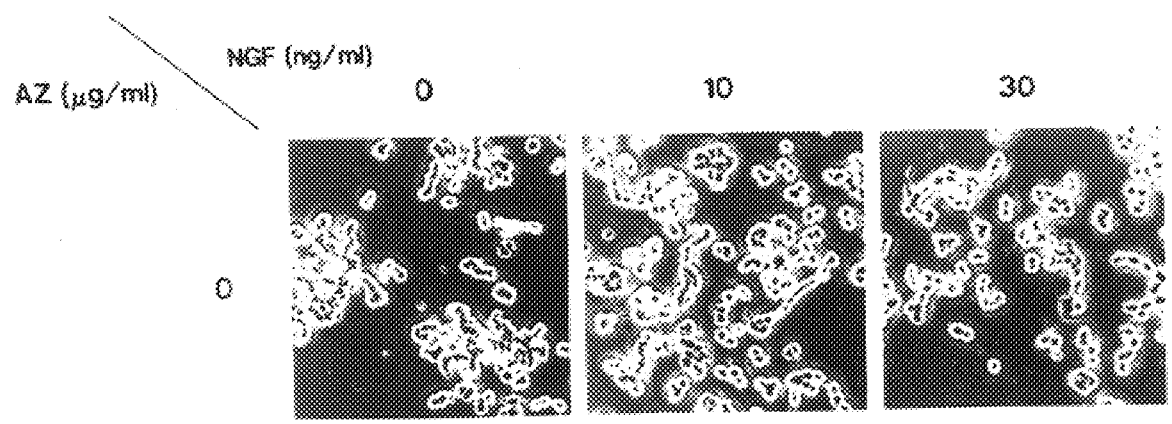
Figures 10D, 10E, 10F:
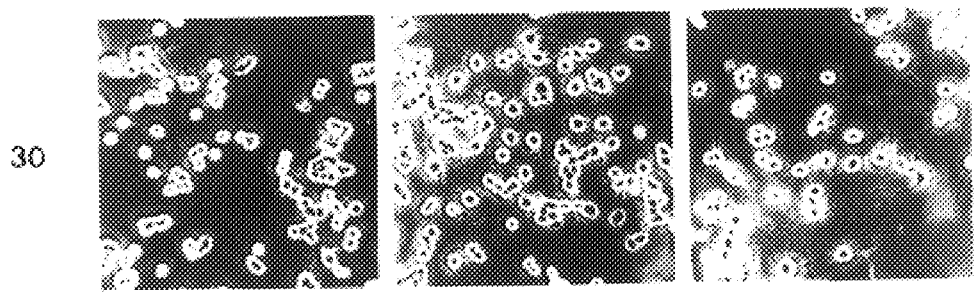

The results are shown in FIGS. 9 and 10.

In FIG. 9, the top panels represent the control group in which FCS alone was added and the bottom panels represent the Compound 1 30 μg/ml group. As seen from the figure, the typical morphological change, i.e. formation of nerve fiber-like processes, is found in the bottom panels as contrasted to the top panels and the most prominent formation of nerve fiber-like processes is observed in the presence of FCS 0.3% (bottom, left). When the concentration of FCS was increased, cells of different shapes appeared (bottom, middle and right). Thus, morphological changes were induced in 30–50% of the total cell population.

In FIG. 10, the top panels represent the NGF alone group (0.3% FCS was added, however) and the bottom panels represent the Compound 1 30 μg/ml group. This figure shows that like the formation of nerve-like processes due to NGF stimulation as seen in the top panels, the formation of nerve-like processes is observed in the Compound 1 group as well. The bottom panels show that the combination of Compound 1 and NGF (however, in the presence of 0.3% FCS) promotes elongation of the process as compared with Compound 1 or NGF alone.

PHARMACOLOGICAL TEST EXAMPLE 12

Effect on hepatic failure

Heat-killed cells of P. acnes (a gift from Dr. Mizoguchi, the Third Department of Internal Medicine, Osaka City University School of Medicine) were administered intravenously in a dose of 3 mg/body to male Balbic mice (7 weeks old, purchased from Japan SLC). Seven days later, a solvent group (0.5% CMC, Dai-ichi Kogyo Seiyaku Co., Ltd) and an untreated group, as well as the test groups given 10 or 100 mg/kg of Compound 1 orally, were provided. One hour after administration of Compound 1, 5 $\mu$g/body of lipopolysaccharide (LPS, Sigma Co., Ltd.) was administered intravenously to induce acute hepatic failure.

The mice in the respective groups were observed for survival rate till 7 days after LPS administration.

The results are shown in FIG. 11.

As the figure shows, the survival rate was 30% for the Compound 1 10 mg/kg group (test group) and 70% for the Compound 1 100 mg/kg group (test group). In contrast, the survival rates for the untreated and solvent groups were 0 and 10%, respectively. These results indicate that Compound 1 exerts a dose-dependent and excellent life-prolonging effect in the model of acute hepatitis.

PHARMACOLOGICAL TEST EXAMPLE 13

Effect of B16 melanoma cells on an experimental model of pulmonary metastasis 16 mouse melanoma cells [Koren, S. and Fleischmann, W. R., J. Interferon Research, 6, 473–482 (198)], $2\times10^6$ cells, were suspended in Eagle's MEM medium (Nissui Pharmaceutical Co., Ltd.) supplemented with 10% FBS (Gibco) to which 3 or 10 $\mu$g/ml of Compound 1 was previously added or not added. The suspension was cultured in a 75-cm$^2$ flask (Corning) in an incubator (National Appliance Model 15300) at 37° C. under 5% carbon dioxide for 4 days. Then, the cells were washed with Dulbecco's PBS solution (Nissui pharmaceutical Co., Ltd.), and 0.05% trypsin (Flow Laboratories) was added to detach the cells from the flask. The cells were washed centrifugally (Hitachi 05PR-22, 1200 rpm, 5 minutes) twice and after addition of 0.2% trypan blue (Wako Pure Chemical Industries Ltd.), viable cells were counted using a hemocytometer (No. J7796, Kayagaki Works) and the cells were diluted with Hank's solution (Flow Laboratories) to a concentration of $5\times10^6$ cells/ml.

The cells obtained as above were transplanted, in a population of $3\times10^5$ cells each, into groups of 7 C57BL/6 mice (7 weeks old, female, purchased from Charles River Japan, Inc.) through the tail vein. Twelve days later, the mice were killed by cervical dislocation and the number of colonies metastatized to the lungs was determined.

The results are shown in FIG. 12 and Table 12 below.

TABLE 12

| Group | No. of colonies in lungs | Mean | SE |
|---|---|---|---|
| Control group | 62, 165, 164, 32, 36, 61 | 86.7 | 25.1 |
| Compound 1 group (3 $\mu$g/ml) | 14, 7, 11, 6, 8, 24, 0 | 10.0* | 2.9 |
| Compound 1 group (10 $\mu$g/ml) | 17, 43, 65, 7, 46, 22, 43 | 34.7 | 7.6 |

*: $P < 0.05$ (Student's t-test)

As seen from the figure and the table, an evident inhibition of pulmonary metastasis was found in both of the groups in which the cells incubated in the medium containing 3 or 10 $\mu$g/ml of Compound 1 were transplanted.

The apoptosis regulating composition of the invention can be effectively used-as a cancer chemotherapeutic agent by virtue of its characteristic apoptosis regulating and cell differentiation inducing activities. The composition is also effective as a therapeutic agent for AIDS, ARC, ATL, other related diseases and HTLV-I-associated diseases by virtue of its antiretrovirus activity, as a therapeutic agent for autoimmune diseases by virtue of its life-span prolonging activity in autoimmune diseases, as a therapeutic agent for thrombocytopenia by virtue of its effect in increasing the expression of platelet associated antigents, as a therapeutic agent for Arzheimer's diseases, as a therapeutic agent for hepatitis by virtue of its life-span prolonging activity in hepatorgy, and as an inhibiting agent of pulmonary metastasis.

What is claimed is:

1. A method for treatment of nephritis which comprises administering to a host afflicted with nephritis an effective amount of at least one carbostyril derivative represented by general formula (1) or a salt thereof:

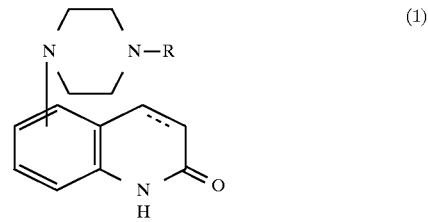

wherein R is a benzoyl group which may optionally be substituted with a lower alkoxy group in the phenyl ring, and the carbon-carbon bond in the 3 and 4 positions of the carbostyril skeleton is a single bond or a double bond.

* * * * *

UNITED STATES PATENT AND TRADEMARK OFFICE
CERTIFICATE OF CORRECTION

PATENT NO. : 5,872,120
DATED : February 16, 1999
INVENTOR(S) : Nakai et al.

It is certified that error appears in the above-identified patent and that said Letters Patent is hereby corrected as shown below:

```
On the Cover Page, in Column 1,
  "[30]      Foreign Application Priority Data
   Jul.  3, 1991    [JP]  Japan .............  3-162587
   Feb. 20, 1992    [JP]  Japan ............   4-33469
   Mar.  3, 1992    [JP]  Japan ............   4-45178
   Mar. 25, 1992    [JP]  Japan ............   4-100585
    Jul. 2, 1992    [JP]  Japan ........  PCT/JP92/00841"
should be
```

UNITED STATES PATENT AND TRADEMARK OFFICE
CERTIFICATE OF CORRECTION

PATENT NO. : 5,872,120
DATED : February 16, 1999
INVENTOR(S) : Nakai et al.

It is certified that error appears in the above-identified patent and that said Letters Patent is hereby corrected as shown below:

```
--    [30]        Foreign Application Priority Data
       Jul.  3, 1991    [JP] Japan .............  3-162587
       Feb. 20, 1992    [JP] Japan .............  4-33469
       Mar.  3, 1--2    [JP] Japan .............  4-45718
       Mar. 25, 1992    [JP] Japan .............  4-100585
       Jul.  2, 1992    [JP] Japan ........  PCT/JP92/00841 --.
```

Signed and Sealed this

Thirty-first Day of August, 1999

Attest:

Attesting Officer

Q. TODD DICKINSON

Acting Commissioner of Patents and Trademarks